United States Patent
Lee et al.

(10) Patent No.: US 10,894,023 B2
(45) Date of Patent: Jan. 19, 2021

(54) ORAL PH INDEPENDENT DOSAGE FORMULATION FOR TREATING NEURODEGENERATIVE DISORDERS

(71) Applicants: Center Laboratories, Inc., Taipei (TW); Medical and Pharmaceutical Industry Technology and Development Center, New Taipei (TW)

(72) Inventors: Meng-Ju Lee, Taipei (TW); Shu-Hsien Chang, Taipei (TW); Chih-Chiang Yang, Taipei (TW); Yuan-Chih Le, New Taipei (TW); Tse-Ching Lin, New Taipei (TW); Ko-Chiang Chen, New Taipei (TW); Lai-Cheng Chin, Taipei (TW); Tai-Yin Ke, New Taipei (TW); Pei-Ying Liao, New Taipei (TW)

(73) Assignee: CENTER LABORATORIES, INC., Taipei (TW)

( * ) Notice: Subject to any disclaimer, the term of this patent is extended or adjusted under 35 U.S.C. 154(b) by 0 days.

(21) Appl. No.: 16/446,634

(22) Filed: Jun. 20, 2019

(65) Prior Publication Data
US 2019/0388340 A1    Dec. 26, 2019

Related U.S. Application Data

(60) Provisional application No. 62/687,317, filed on Jun. 20, 2018.

(51) Int. Cl.
| | | |
|---|---|---|
| A61K 31/13 | (2006.01) | |
| A61K 31/445 | (2006.01) | |
| A61K 9/16 | (2006.01) | |
| A61K 9/50 | (2006.01) | |
| A61K 9/48 | (2006.01) | |
| A61K 9/00 | (2006.01) | |
| A61P 25/16 | (2006.01) | |
| A61P 25/14 | (2006.01) | |
| A61P 25/28 | (2006.01) | |

(52) U.S. Cl.
CPC ............ *A61K 31/13* (2013.01); *A61K 9/0053* (2013.01); *A61K 9/1652* (2013.01); *A61K 9/1676* (2013.01); *A61K 9/4858* (2013.01); *A61K 9/4866* (2013.01); *A61K 9/5084* (2013.01); *A61K 31/445* (2013.01); *A61P 25/14* (2018.01); *A61P 25/16* (2018.01); *A61P 25/28* (2018.01)

(58) Field of Classification Search
None
See application file for complete search history.

(56) References Cited

U.S. PATENT DOCUMENTS

2011/0171302 A1* 7/2011 Shane .................. A61K 9/5078
424/467

\* cited by examiner

*Primary Examiner* — Sin J Lee

(57) ABSTRACT

Disclosed herein is an oral dosage formulation suitable for treating a neurodegenerative disorder. The oral dosage formulation contains both sustained-release and immediate-release drugs. The sustained-release drug in the oral dosage formulation is memantine, and the immediate-release drug in the oral dosage formulation is donepezil and/or memantine, and the formulation is characterized in having a pH-independent dissolution profile of memantine at a pH range from about 1.0 to about 7.0.

3 Claims, 2 Drawing Sheets

ORAL PH INDEPENDENT DOSAGE FORMULATION FOR TREATING NEURODEGENERATIVE DISORDERS

CROSS REFERENCES

This application claims priority to U.S. Provisional Patent Application Ser. No. 62/687,317, filed Jun. 20, 2018, the content of which is hereby incorporated by reference in its entirety.

BACKGROUND OF THE INVENTION

1. Field of the Invention

The present disclosure in general relates to oral dosage formulation suitable for treating neurodegenerative disorders. More specifically, the present disclosure relates to oral pH independent dosage formulations that comprise drugs in immediate-release and sustained-release portions.

2. Description of Related Art

Oral drug delivery in the form of conventional dosage forms has been adopted since long, among them, solid oral dosage forms account to cover major market share owing to their versatility. To attain optimum clinical performance, many drugs are formulated as controlled release dosage forms. However, formulating weakly acidic or basic drugs as sustained-release dosage forms faces some development challenges, such as poor solubility, pH-dependent solubility, incomplete drug release, just to name a few. Accordingly, there is a need to develop pH independent drug delivery system to overcome the afore-indicated limitations.

SUMMARY

The present study aims at overcoming pH-dependent solubility problem observed in controlled release dosage forms.

In one aspect, the present disclosure is directed to an oral dosage formulation suitable for treating a neurodegenerative disorder, such as dementia, Alzheimer's disease, Parkinson's disease, Huntington's disease and the like central nervous system (CNS) disorder. The oral dosage formulation comprises a sustained-release portion of memantine and an immediate-release portion of donepezil and/or memantine, and is characterized in having a pH-independent dissolution profile of memantine from about pH 1.0 to 7.2. According to preferred embodiments, the oral dosage formulation is characterized in having a pH-independent dissolution profile of memantine at the range of pH from about 1.2 and about 6.8.

According to embodiments of the present disclosure, the sustained-release portion of memantine is in the form of granules (i.e., SR memantine granules). Each SR memantine granules comprises in its structure, a memantine pellet, a sustained-release film coated on the memantine pellet. According to optional embodiments, the sustained-release film coated memantine pellet may further comprise an immediate-release layer of memantine coated thereon.

According to embodiments of the present disclosure, the immediate-release portion of donepezil and/or memantine are in the form of granules (i.e., IR donepezil granules and/or IR memantine granules). Each IR donepezil granules is composed of a donepezil pellet, and each IR memantine granules is composed of a memantine pellet.

According to some embodiments of the present disclosure, the oral dosage formulation provides an average blood level $C_{max}$ of memantine in a range of about 17-25 ng/mL during an average $T_{max}$ of about 15.5 hours, and an average blood level $C_{max}$ of the donepezil in a range of about 6-13 ng/mL during an average $T_{max}$ of about 2.5 hours. The formulation exhibits an $AUC_{0-t}$ of memantine in a range of about 1747-2258 ng·h/mL and an $AUC_{0-t}$ of donepezil in a range of about 450-704 ng·h/mL, respectively measured after 324 hours.

According to other embodiments of the present disclosure, the oral dosage formulation provides an average blood level $C_{max}$ of memantine in a range of about 19-32 ng/mL during the average $T_{max}$ of about 14.33 hours, and the average blood level $C_{max}$ of donepezil is in a range of about 6.5-12.5 ng/mL during the average $T_{max}$ of about 2 hours. The formulation exhibits an $AUC_{0-t}$ of memantine in a range of about 1630-3000 ng·h/mL and an $AUC_{0-t}$ of donepezil in a range of about 279-499 ng·h/mL, respectively measured after 324 hours.

According to some embodiments of the present disclosure, memantine, a salt, a solvate, or a mixture thereof is present in an amount of about 20 mg in the oral formulation, whereas donepezil is present in an amount of about 5 mg in the oral formulation.

To produce the oral formulation of this invention, the SR granules and the IR granules are mixed together and are then used to fill up capsules.

According to the principles and spirits of the present disclosure, the oral dosage formulation may be formulated to meet the steady state blood levels required for the treatment of the neurodegenerative disorder.

Moreover, according to embodiments of the present disclosure, the oral dosage formulation may be administered once a day or once every two days, which is advantageous at least in terms of patient compliance.

By administering a patient the present oral dosage formulation on a daily (once per day) or bi-daily (once every two days) basis, the course of a treatment for a subject with a neurodegenerative disorder such as dementia or Alzheimer's disease is greatly simplified thereby enhancing the patient compliance. For example, the number of capsules the subject required to take daily may be substantially reduce to a significantly low number of one or one capsule for every two days, in accordance with some examples of this disclosure. Also, by respectively providing adequate amounts of donepezil and memantine in the sustained-release and the immediate-released portions, it is possible to achieve the desired therapeutic effect as well as ameliorate the side effects experienced by the patient.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The present description will be better understood from the following detailed description read in light of the accompanying drawings, where.

DESCRIPTION OF THE INVENTION

Figure 1A:
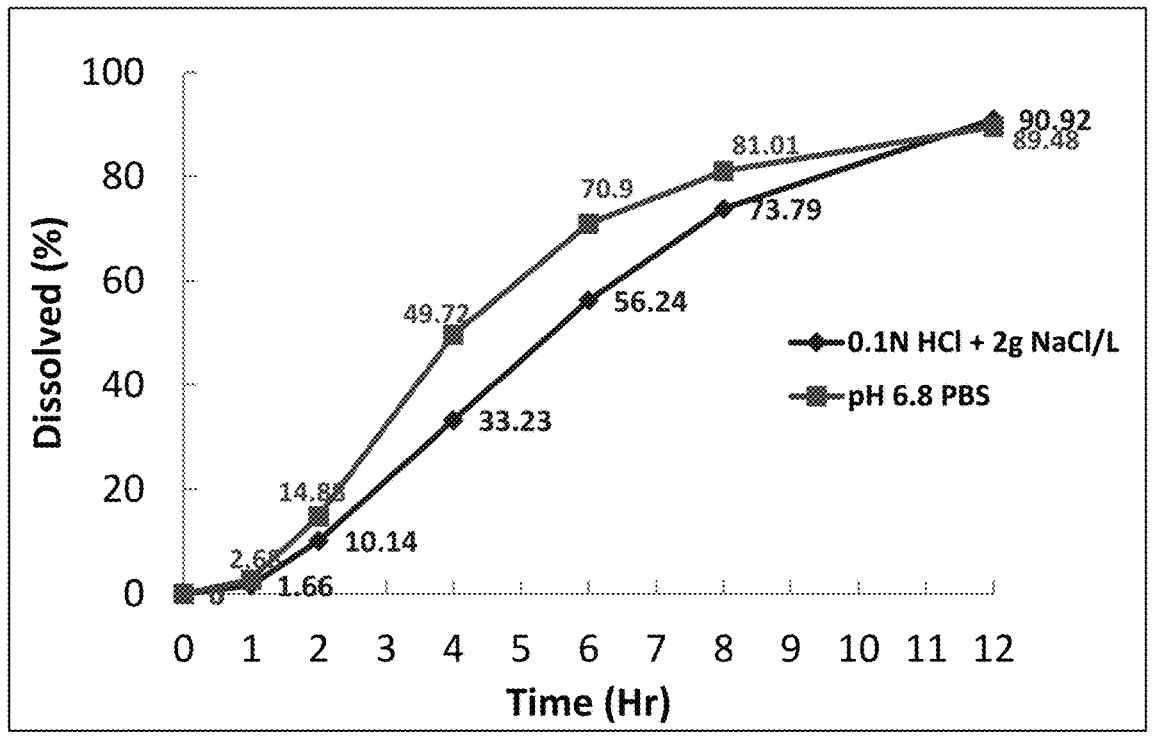
FIGS. 1A and 1B are dissolution profiles of SR-film coated memantine pellets of example 1.2.2 and memantine IR/SR granules of example 1.2.3 of the present disclosure.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The practices of this invention are hereinafter described in detail with respect to a method for treating a patient suffering from a neurodegenerative disorder with an oral dosage formulation. Results of pilot pharmacokinetic study, as described hereinbelow, show that the oral dosage formulation, particularly, an oral dosage formulation that contains both immediate-release (IR) and sustained-release (SR) drugs, in which the dissolution profile is pH independent, i.e., the release profile of the memantine IR/SR granules does not change with its surrounding pH from about 1.0 to 7.2, preferably from about pH 1.2 to 6.8.

As used in the present disclosure, the term "$C_{max}$" refers to the maximum concentration of an active compound or drug (e.g., memantine or donepezil) in the blood plasma, whereas the term "$T_{max}$" means the time to achieve the maximum plasma concentration of said active compound or drug. The term "$AUC_{0-t}$" refers to an area under the curve from zero to the last measured time point of a measurable drug concentration. The term "mean residence time (MRT)" refers to average time for a drug molecules to reside in the body.

In accordance with some embodiments of the present disclosure, the oral dosage formulation provides an average blood level $C_{max}$ of memantine in a range of about 17-25 ng/mL during an average $T_{max}$ of about 15.5 hours, and an average blood level $C_{max}$ of the donepezil in a range of about 6-13 ng/mL during an average $T_{max}$ of about 2.5 hours.

In accordance with other embodiments of the present disclosure, the average blood level $C_{max}$ of memantine is in a range of about 19-32 ng/mL during the average $T_{max}$ of about 14.33 hours, and the average blood level $C_{max}$ of donepezil is in a range of about 6.5-12.5 ng/mL during the average $T_{max}$ of less than about 2 hours.

In pharmacokinetic (PK) studies, $AUC_{0-t}$ of the active compound or drug is often used for assessing the efficacy or the bioequivalence of the active compound/drug. In accordance with the present disclosure, the blood level of the active compound is last measured at 324 hours after the ingestion of the oral dosage formulation. In accordance with some embodiments of the present disclosure, the formulation may provide an $AUC_{0-t}$ of memantine in a range of about 1747-2258 ng·h/mL and an $AUC_{0-t}$ of donepezil in a range of about 450-704 ng·h/mL, respectively measured after 324 hours. In other embodiments, the formulation may provide an $AUC_{0-t}$ of memantine in a range of about 1630-3000 ng·h/mL and an $AUC_{0-t}$ of donepezil in a range of about 279-499 ng·h/mL, respectively measured after 324 hours.

Memantine hydrochloride is currently sold under various brand names including EBIXA® and NAMENDA®. For daily dosage containing more than 5 mg of memantine hydrochloride, it is generally advised that the formulation shall be administered twice daily. For example, if the patient is prescribed to take 15 mg of memantine hydrochloride daily, he/she is advised to take a dose of 10 mg in the morning and a dose of 5 mg in the afternoon. According to embodiments of this disclosure, total daily dosage of memantine hydrochloride is 20 mg/day. The oral dosage formulation of the present disclosure may be administered once a day or once every two days according to the present methods. In this regard, the method according to embodiments of the present disclosure may advantageously simplify the course of the treatment while reduce the occurrence and/or severity of at least one of the side effects.

As used herein, the term "salt" refers herein as a salt which is formed by the interaction of a base (such as memantine or donepezil in this disclosure) with an acid, including organic or inorganic types of acids such as hydrochloric acid, hydrobromic acid, hydroiodic acid, perchloric acid, methylsulfonic acid, sulfuric acid, nitric acid, phosphoric acid, acetic acid, propionic acid, glycolic acid, pyruvic acid, malonic acid, succinic acid, maleic acid, fumaric acid, tartaric acid, citric acid, benzoic acid, carbonic acid, cinnamic acid, methanesulfonic acid, ethanesulfonic acid, hydroxyethanesulfonic acid, benzenesulfonic acid, p-toluene sulfonic acid, cyclohexanesulfamic acid, salicyclic acid, p-aminosalicyclic acid, 2-phenoxybenzoic acid and 2-acetoxybenzoic acid. In one preferred example, the salt is memantine hydrochloride. In another example, the salt is donepezil hydrochloride. The term "solvate" herein refers to a complex formed by the interaction of a compound (such as memantine or donepezil in this disclosure) with surrounding solvent molecules, such as water, ethanol, and etc. In one example, the solvate of a first compound is a memantine hydrate.

The term "sustained-release" herein refers to the release of the therapeutic compound occurs over an extended period of time leading to lower peak plasma concentrations and/or is directed to a prolonged $T_{max}$ as compared with "immediate-release" portion containing the same compound. The sustained-release portion of the dosage formulation is designed to deliver memantine, a salt, or a solvate thereof to the digestive system of a subject continuously over a period of time for at least an hour and preferably more than several hours. In one example, the dissolution rate is slow enough that at least about 50% of memantine, a salt or a solvate thereof remains unreleased after two hours. In general, the memantine, a salt, or a solvate thereof will be at least 89% released within 12 hours.

According to embodiments of the present disclosure, the release of memantine HCl from the present oral formulation is independent to the change in the surrounding pH value, or the amount of memantine HCl released from the formulation in acidic condition is comparable to that in basic condition. According to embodiments of the present disclosure, the oral formulation has a pH-independent dissolution profile of memantine HCl from about pH 1.0 to 7.2, such as 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1 and 7.2; preferably, from about pH 1.2 to 6.8, such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, and 6.8.

The memantine, a salt or a solvate thereof in the sustained-release portion of the formulation may in the form of sustained-release fine particles or pellets that are produced by any known method such as wet granulation, dry granulation or fluid bed method. In one example, the sustained-release fine particles or pellets are produced by fluid bed method, which in general involves the steps of mixing the drug, a starter core (e.g., a Sugar Sphere or a matrix polymer), and a binder solution; spraying and curing the pellets; and screening through a suitable sieve to produce particles with desired sizes. Examples of the starter core include, but are not limited to, Sugar Sphere, methylcellulose (MC), ethyl cellulose (EC), hydroxypropyl cellulose (HPC), hydroxypropyl methylcellulose (HPMC), carboxyl methylcellulose (CMC), microcrystalline cellulose, cellulose acetate, cellulose propionate, cellulose acetate propionate, cellulose acetate butyrate, cellulose acetate phthalate, cellulose triacetate, polymethyl methacrylate, polyethyl methacrylate, polyvinyl alcohol, polyvinyl acetate, polyvinyl alcohol-ethylene glycol, carbomer, polyethylene glycol (PEG) and a combination thereof. Suitable starter core(s) are those sold under the trademark that includes, but is not limited to, SUGLETS®, VIVAPHARM®, CELPHERE® CP708, EUDRAGIT®, OPADRY®, ACRYL-EZE®, SURELEASE®, VIVAPHARM®, METHOCEL®, ETHOCEL®, or SURETERIC®.

Useful binders include, but are not limited to, acacia, tragacanth, alginic acid, sodium alginate, carbomer, carboxymethylcellulose sodium, carrageenan, cellulose acetate phthalate, *ceratonia*, copovidone, dextrates, dextrin, dextrose, methylcellulose, ethylcellulose, carboxymethyl cellulose, hydroxypropyl methyl cellulose, hydroxyethyl cellulose; hydroxyethylmethyl cellulose; hydroxypropyl cellulose; hydroxypropyl starch; hypromellose, gelatin, starch, sucrose, lactose, magnesium aluminum silicate, maltodextrin, maltose, microcrystalline cellulose, polyvinyl pyrrolidone, polyacrylamide, povidone and pregelatinized starch. In certain examples, the sustained-release pellet is prepared by mixing memantine, a salt, a solvate or a mixture thereof with a sugar sphere made of sucrose and starch, and at least one matrix polymer to form pellets that contain memantine. Examples of the matrix polymer include, but are not limited to, methylcellulose (MC), ethyl cellulose (EC), hydroxypropyl cellulose (HPC), hydroxypropyl methylcellulose (HPMC), carboxyl methylcellulose (CMC), microcrystalline cellulose, cellulose acetate, cellulose propionate, cellulose acetate propionate, cellulose acetate butyrate, cellulose acetate phthalate, cellulose triacetate, polymethyl methacrylate, polyethyl methacrylate, polyvinyl alcohol, polyvinyl acetate, polyvinyl alcohol-ethylene glycol, carbomer, polyethylene glycol (PEG) and a combination thereof. Then, each of the memantine containing pellets is coated with a sustained-release film to produce the sustained-release film coated memantine pellets. In some examples, the sustained-release film contains at least one matrix polymer described above (e.g., HPMC). In other examples, the sustained-release film contains at least one matrix polymer and titanium dioxides.

Other useful diluents include, but are not limited to, ammonium alginate, calcium carbonate, calcium phosphate dibasic, calcium phosphate tribasic, calcium sulfate, cellulose, cellulose acetate, compressible sugar, dextrates, dextrin, dextrose, erythritol; ethylcellulose, fructose, fumaric acid, glyceryl palmitostearate, lactitol, lactose, mannitol, magnesium carbonate, magnesium oxide, maltodextrin, maltose, microcrystalline cellulose, polydextrose, polymethacrylates, sodium chloride, sorbitol, starch, sucrose, ARBOCEL A300®; LUDIPRESS®; and SUPER TAB®.

Optionally, the SR-filmed coated pellets may be further coated with an immediate release (IR) layer of memantine. The SR coating and the IR layer may be applied as a film respectively deposited over the sustained-release pellets and the sustained-release film coated pellets, by any known techniques such as spraying, dipping, or pan-coating, thereby forming the SR granules.

The immediate-release portion of the dosage formulation is designed to rapidly disintegrate upon contacting a fluid such as water and allow fast leaching out of donepezil or memantine to the environment continuously over a short period of time, such as several minutes or in an hour. The dissolution rate is fast enough that at least 80% of donepezil is released within the first 5 minutes. In general, at least 95% of donepezil will be released within 10 minutes.

In one example, the immediate-release portion comprises donepezil, which is in a form of an immediate-release granule. In another example, the immediate-release portion comprises donepezil and memantine, respectively in the form of immediate-release granules.

The immediate-release granules may be produced by any known method, such as dry or wet granulation method as described above. In one example, donepezil or memantine is mixed with disintegrants and/or binders, and adsorbents and then the mixture is subjected to either fluid bed granulation or spray drying to produce particles with desired immediate-release property. Examples of disintegrants include, but are not limited to, cross-linked polyvinyl pyrrolidone or crospovidone, starch derivatives such as carboxymethyl cellulose and cellulose derivatives; calcium alginate; carboxymethylcellulose calcium; carboxymethylcellulose sodium; croscarmellose sodium; docusate sodium; hydroxypropyl cellulose; magnesium aluminum silicate; methylcellulose; polacrilin potassium; sodium alginate; sodium starch glycolate and pregelatinized starch. Examples of adsorbents include, but are not limited to, aluminum hydroxide adjuvant; aluminum oxide; aluminum phosphate adjuvant; attapulgite; bentonite; powdered cellulose; colloidal silicon dioxide; hectorite; kaolin; magnesium aluminum silicate; magnesium carbonate; microcrystalline cellulose; pectin; polycarbophil; and saponite. At least 50% of the immediate-release granules thus prepared have a size that may pass an 80-mesh sieve; preferably, a 60-mesh sieve; more preferably, a 40-mesh sieve; and most preferably, a 20-mesh sieve.

According to some embodiments, the oral dosage formulation is in a form of capsule containing therein both the sustained-release granules of memantine (i.e., memantine, a salt, a solvate, or a mixture thereof) and the immediate-release granules of donepezil (i.e., a salt or a solvate thereof, an enantiomer thereof, a salt or a solvate of the enantiomer or a mixture thereof). According to other embodiments, the oral dosage formulation is in a form of capsule containing therein both the sustained-release granules of memantine (i.e., memantine, a salt, a solvate, or a mixture thereof) and the immediate-release granules of donepezil (i.e., a salt or a solvate thereof, an enantiomer thereof, a salt or a solvate of the enantiomer or a mixture thereof) and memantine (i.e., memantine, a salt, a solvate, or a mixture thereof).

According to the methods of the present disclosure, the oral dosage formulations described herein are administered to a patient at therapeutically effective doses, preferably, with minimal toxicity. Specific examples of the oral dosage formulation of this disclosure include about 1-30 mg of memantine, a salt, a solvate or a mixture thereof, such as 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 mg, preferably about 5-20 mg of memantine, a salt, a solvate or a mixture thereof, such as 5, 6, 7, 8, 9, 10, 11, 12, 13, 14, 15, 16, 17, 18, 19, and 20 mg; and about 1-20 mg of donepezil, a salt or a solvate thereof, an enantiomer thereof, a salt or a solvate of the enantiomer or a mixture thereof, such as 1, 2, 3, 4, 5, 6, 7, 8, 9, 10, 11, 12, 13, 14, 15, 16, 17, 18, 19, 20 mg, preferably about 5-18 mg of donepezil, a salt or a solvate thereof, an enantiomer thereof, a salt or a solvate of the enantiomer or a mixture thereof, such as 5, 6, 7, 8, 9, 10, 11, 12, 13, 14, 15, 16, 17, and 18 mg. In one example, memantine, a solvate or a mixture thereof is present in an amount of about 20 mg/dosage formulation, and donepezil, a salt or a solvate thereof, an enantiomer thereof, a salt or a solvate of the enantiomer or a mixture thereof is present in an amount of about 5 mg/dosage formulation.

It must be noted that as used herein and in the appended claims, the singular forms "a", "an", and "the" include plural referents unless the context clearly dictates otherwise. As used herein, the term "about" refers to a range of values+ 10% of a specified value. For example, the phrase "about 5 mg" includes±10% of 5 mg, or from 4.5 to 5.5 mg.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

The following Examples are provided to illustrate certain aspects of the present invention and to aid those of skilled in the art in practicing this invention. These Examples are in no way to be considered to limit the scope of the invention in any manner.

EXAMPLES

Example 1 Production of Donepezil/Memantine Oral Formulations

In this example, the donepezil IR granules and memantine IR/SR granules were independently produced in accordance with steps and conditions described in examples 1.1 to 1.3. The thus produced granules were then used to fill a capsule in accordance with the conditions set forth in example 1.4 thereby forming the donepezil/memantine oral formulation.

1.1 Donepezil IR Granules

Briefly, donepezil (50 g), microcrystalline cellulose (AVICEL PH105, 850 g) and starch 1500 (100 g) were mixed and passed a 40-mesh sieve, the mixture was further mixed in super mixer (high shear force) with the impeller and chopper respectively set at a speed of 150 and 1,800 rpm for about 30 sec. Then, the chopper speed was reduced to about 150 rpm, and water (450 mL) was added gradually to form wet granules that passed a 20-mesh sieve. The granules were subsequently dried at 50° C., and passed another 18-mesh sieve. The granules thus produced had a water content of less than 5%.

1.2 Memantine IR/SR Granules

To produce the memantine IR/SR granules, memantine pellets was first formed, followed by coating each pellets with a sustained release film (i.e., SR-film) and another IR layer of memantine.

1.2.1 Memantine Pellets

The memantine pellets were produced by mixing ingredients of Table 1 in a bottom spray fluid bed under processing parameters set as follows:

| Processing Parameters for Forming Memantine Pellet | |
| --- | --- |
| Spray gun diameter | 1.0 mm |
| Air Pressure in the spray gun | 2.3 bar |
| Pump | 6-8% |
| Inlet Temperature | 35-37° C. |
| Exhaust temperature | 25° C. |
| volume | 70 (m$^3$/h) |
| Product temperature | 28-30° C. |
| Shaking duration | 10 sec |

1.2.2 SR-Film Coated Memantine Pellets

Each of the memantine pellets was coated with a sustained-release film (i.e., SR film) by use of an SR-coating formulation-1 of Table 1. The processing parameters for coating SR-coating formulation-1 onto the memantine pellets are set forth as follows:

| Processing Parameters for Forming SR-Film Coated Memantine Pellet | |
| --- | --- |
| Spray gun diameter | 1.0 mm |
| Air Pressure in the spray gun | 2.0 bar |
| Pump | 5-8% |
| Inlet Temperature | 55° C. |
| Exhaust temperature | 35° C. |
| volume | 70 (m$^3$/h) |
| Product temperature | 40-42° C. |
| Shaking duration | 10 sec |

1.2.3 Memantine IR/SR Granules

Each of the SR-film coated memantine pellets of example 1.2.2 was further coated with an IR layer of memantine by use of an IR-coating formulation-1 listed in Table 1. The processing parameters for coating IR-coating formulation-1 onto the the SR-film coated pellets are set forth as follows:

| Processing Parameters for Forming IR-Layer Coated Memantine Granule | |
| --- | --- |
| Spray gun diameter | 1.0 mm |
| Air Pressure in the spray gun | 2.2 bar |
| Pump | 5-6% |
| Inlet Temperature | 34-35° C. |
| Exhaust temperature | 25° C. |
| volume | 70 (m$^3$/h) |
| Product temperature | 29-30° C. |
| Shaking duration | 10 sec |

TABLE 1

| Compositions of memantine IR/SR Granules | |
| --- | --- |
| Ingredients | Weight (g)/Volume (mL) |
| Memantine Pellet Formulation | |
| Sugar sphere | 600 g |
| Memantine HCl | 120 g |

TABLE 1-continued

Compositions of memantine IR/SR Granules

| Ingredients | Weight (g)/Volume (mL) |
|---|---|
| HPMC E6 | 60 g |
| PEG 8000 | 12 g |
| water | 600 mL |
| *SR-Coating Formulation-1* | |
| Memantine pellet | 350 g |
| SURELEASE ® | 308 g |
| water | 205 mL |
| *IR-Coating Formulation-1* | |
| SR-film coated memantine pellet | 350 |
| Memantine HCl | 30.05 |
| HPMC E6 | 15.03 |
| water | 150 mL |

HPMC E6 = hydroxypropyl methyl cellulose
PEG 8000 = polyethylene glycol 8000
MCC = microcrystalline cellulose 1.3 Memantine IR/SR Granules In this example, memantine IR/SR granules were produced in accordance with procedures described in example 1.2, except the memantine pellets of example 1.2.1 were respectively coated with a sustained-release film (i.e., SR film) and an IR layer in accordance with SR-coating and IR-coating formulations slightly different from those listed in Table 1.

1.3.1 SR-Film Coated Memantine Pellets

Each of the memantine pellets of example 1.2.1 was coated with a sustained-release film (i.e., SR film) in accordance with the procedures described in example 1.2.2, except an SR-coating formulation-2 of Table 2 was used instead.

1.3.2 Memantine IR/SR Granules

Each of the SR-film coated memantine pellets of example 1.3.1 was further coated with an IR layer in accordance with the procedures described in example 1.2.3, except an IR-coating formulation-2 listed in Table 2 was used.

TABLE 2

Composition of memantine IR/SR Granules

| Ingredients | Weight (g)/Volume (mL) |
|---|---|
| *Memantine Pellet Formulation* | |
| Sugar sphere | 600 g |
| Memantine HCl | 120 g |
| HPMC E6 | 60 g |
| PEG 8000 | 12 g |
| water | 600 mL |
| *SR-Coating Formulation-2* | |
| Memantine pellet | 350 g |
| SURELEASE ® | 224 g |
| water | 149 mL |
| *IR-Coating Formulation-2* | |
| SR-film coated memantine pellet | 350 |
| Memantine HCl | 31.95 |
| HPMC E6 | 15.98 |
| water | 150 mL |

HPMC E6 = hydroxypropyl methyl cellulose
PEG 8000 = polyethylene glycol 8000
MCC = microcrystalline cellulose 1.4 Production of Donepezil/Memantine Oral Formulations 1 and 2

The donepezil IR granules of example 1.1 and the memantine IR/SR granules of examples 1.2 or 1.3 were respectively weighted and filled gelatin capsules to produce the oral formulations 1 and 2, with ingredients respectively listed in Tables 3 and 4.

TABLE 3

Composition of donepezil/memantine oral formulation 1

| | Ingredients | Weight (mg) | Percentage (%) |
|---|---|---|---|
| Memantine IR/SR granules of Example 1.2 | Memantine HCl | 20 | 16.35 |
| | Sugar sphere | 73.53 | 60.12 |
| | HPMC | 9.32 | 7.62 |
| | PEG 8000 | 1.31 | 1.11 |
| | Ethyl cellulose aqueous solution | 18.16 | 14.80 |
| | Subtotal | 122.32 | 100 |
| Donepezil IR granules of Example 1.1 | Donepezil HCl | 5 | 5 |
| | microcrystalline cellulose (AVICEL PH105) | 85 | 85 |
| | Starch 1500 | 10 | 10 |
| | Subtotal | 100 | 100 |

TABLE 4

Composition of donepezil/memantine oral formulation 2

| | Ingredients | Weight (mg) | Percentage (%) |
|---|---|---|---|
| Memantine IR/SR granules of Example 1.3 | Memantine HCl | 20 | 16.58 |
| | Sugar sphere | 73.55 | 62.63 |
| | HPMC | 9.98 | 8.27 |
| | PEG 8000 | 1.40 | 1.16 |
| | Ethyl cellulose aqueous solution | 13.7 | 11.36 |
| | Subtotal | 120.63 | 100 |
| Donepezil IR granules of Example 1.1 | Donepezil HCl | 5 | 5 |
| | microcrystalline cellulose (AVICEL PH105) | 85 | 85 |
| | Starch 1500 | 10 | 10 |
| | Subtotal | 100 | 100 |

Example 2 Production of Donepezil/Memantine Oral Formulation 3

In this example, the donepezil/memantine IR granules and memantine SR granules were independently produced in accordance with steps and conditions described in examples 2.1 and 2.2. The thus produced granules were then used to fill a capsule thereby forming an oral formulation in accordance with the conditions set forth in example 1.4.

2.1 Donepezil/Memantine IR Granules

Briefly, donepezil (7.94 g), memantine HCl (12 g) MCC PH-101 (128.41 g) and starch 1500 (15 g) were mixed and passed a 40-mesh sieve, and the mixture was mixed in super mixer with the impeller set at a speed of 170 rpm for about 2 min. Then, water (80 g) was slowly added into the mixture within 10-30 sec while granulation took place in the super mixer with the impeller and chopper respectively set at a speed of 270 and 2,700 rpm for a total time of 4 min. Then, the wet granules were passed through a 16-mesh sieve, and dried at 50° C. in an oven until the water content was reduced to less than 6%. At last, the dried granules were passed through a 20-mesh sieve and mix with 40-mesh-sieved magnesium stearate (1.65 g).

2.2 Memantine SR Granules

To produce the memantine SR granules, memantine pellets of example 1.2.1 were respectively coated with a sustained release film (i.e., SR-film) by use of the SR-coating formulation-2 of example 1.3.1.

2.3 Production of Donepezil/Memantine Oral Formulation 3

The donepezil/memantine IR granules of example 2.1 and the memantine SR granules of example 2.2 were respectively weighted and filled gelatin capsules to produce the oral formulation 3, with ingredients listed in Table 5.

TABLE 5

Composition of oral formulation 3

|  | Ingredients | Weight (mg) | Percentage (%) |
|---|---|---|---|
| donepezil/memantine IR granules of example 2.1 | Donepezil HCl† | 5 | 4.5 |
|  | Memantine HCl | 8 | 7.3 |
|  | MCC PH-101 | 85.9 | 78.1 |
|  | Pregelatinized Starch 1500 | 10.0 | 9.1 |
|  | Magnesium stearate | 1.1 | 1 |
|  | Subtotal | 110 | 100 |
| memantine SR granules of example 2.2 | Memantine HCl | 12 | 13.06 |
|  | Sugar sphere | 60 | 65.29 |
|  | HPMC E6 | 6 | 6.53 |
|  | PEG 8000 | 1.2 | 1.31 |
|  | SURELEASE ® | 12.7 | 13.82 |
|  | Subtotal | 91.9 | 100 |

†The water content of donepezil HCl was 5.5%.

Example 3 In Vitro Dissolution Profiles of the Pellets, Granules and Formulations of Examples 1 and 2

The in vitro dissolution profiles of the pellets, granules and formulations in examples 1 and 2 were obtained at various acidic conditions. Specifically, the dissolution tests were performed at a temperature of 37° C. in solutions respectively having pH 1.2, 4.5 and 6.8, which simulated the physiological conditions in the stomach and small intestine. Samples of dissolution media were collected at predetermined intervals and analyzed by high performance liquid chromatography (HPLC) to obtain the dissolution profile.

3.1 Dissolution Profiles of SR-Film Coated Memantine Pellets of Example 1.2.2 and Memantine IR/SR Granules of Example 1.2.3

Figure 1B:
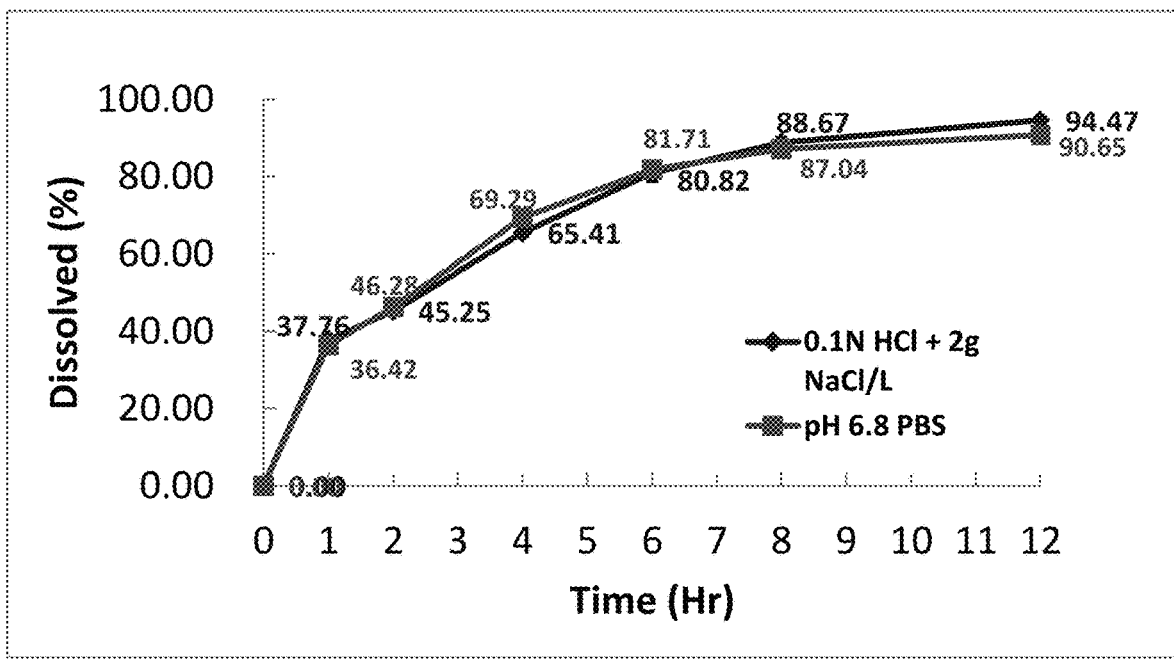

Dissolution profiles of the SR-film coated memantine pellets of example 1.2.2 at pH 1.2 and 6.8 is summarized in Table 6. It appeared that less than 20% of memantine were released within 2 hrs in the SR-filmed coated pellets, and over 80% were released after 8 hrs. Most interestingly, the release of memantine was pH-dependent, in which the basic condition (i.e., pH 6.8) appeared to promote the release of memantine from the SR-film coated pellets, as compared to that in the acidic condition (i.e., pH 1.2) (see Table 6 and FIG. 1A). The pH-dependent dissolution phenomenon diminished after the SR-film coated pellets were further coated with another layer of memantine to form memantine IR/SR granules (see Table 7 and FIG. 1B).

TABLE 6

In vitro dissolution profile of the SR-film coated memantine pellets of example 1.2.2

| T (hr) | pH 1.2 Mean Diss, % | pH 6.8 Mean Diss, % |
|---|---|---|
| 1 | 1.66 | 2.68 |
| 2 | 10.14 | 14.88 |
| 4 | 33.23 | 49.72 |
| 6 | 56.24 | 70.90 |
| 8 | 73.79 | 81.02 |
| 12 | 90.92 | 89.48 |

TABLE 7

In vitro dissolution profile of the memantine IR/SR granules of example 1.2.3

| T (hr) | pH 1.2 Mean Diss, % | pH 6.8 Mean Diss, % |
|---|---|---|
| 1 | 37.76 | 36.42 |
| 2 | 45.25 | 46.28 |
| 4 | 65.41 | 69.29 |
| 6 | 80.82 | 81.71 |
| 8 | 88.67 | 87.04 |
| 12 | 94.47 | 90.65 |

3.2 Dissolution Profiles of SR-Film Coated Memantine Pellets of Example 1.3.1 and Memantine IR/SR Granules of Example 1.3.2

Figure 2A:
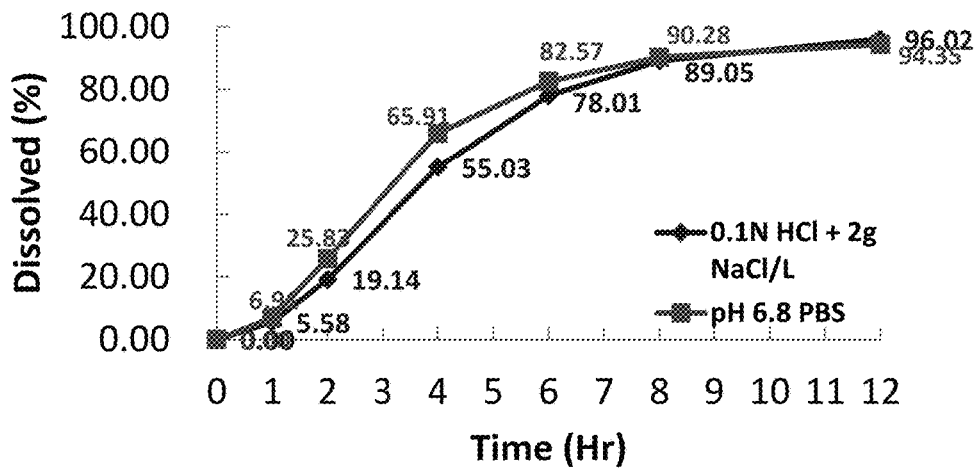
FIGS. 2A and 2B are dissolution profiles of SR-film coated memantine pellets of example 1.3.1 and memantine IR/SR granules of example 1.3.2 of the present disclosure.
Figure 2B:
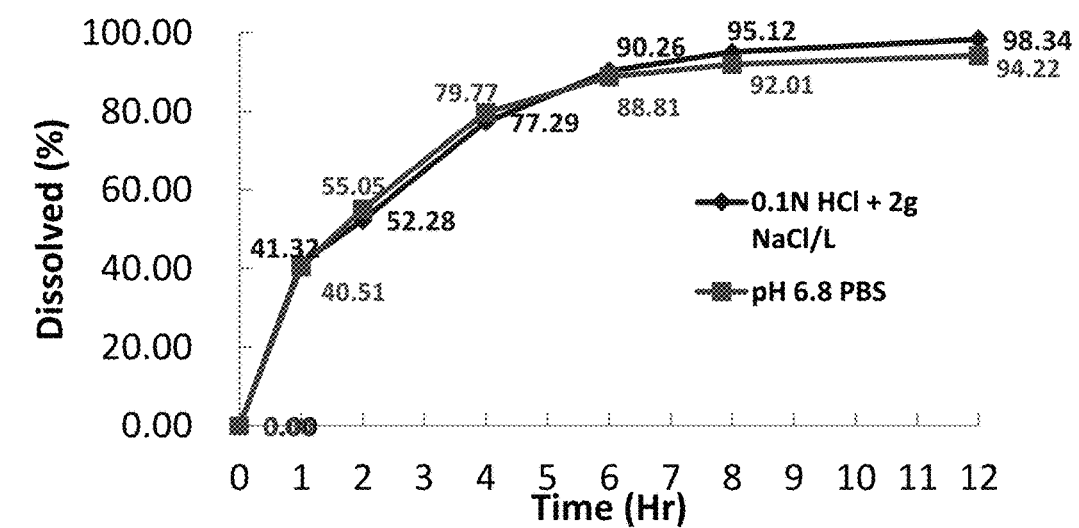

Dissolution profiles of the SR-film coated memantine pellets of example 1.3.1 at pH 1.2 and 6.8 is summarized in Table 8. Similar to the finding in Table 6, the release of memantine also appeared to be pH-dependent, in which the basic condition (i.e., pH 6.8) also appeared to promote the release of memantine from the SR-film coated pellets, as compared to that in the acidic condition (i.e., pH 1.2) (Table 8 and FIG. 2A). The pH-dependent dissolution phenomenon diminished after the SR-film coated pellets were further coated with another layer of memantine to form memantine IR/SR granules (Table 9 and FIG. 2B).

TABLE 8

In vitro dissolution profile of the SR-film coated memantine pellets of example 1.3.1

| T (hr) | pH 1.2 Mean Diss, % | pH 6.8 Mean Diss, % |
|---|---|---|
| 1 | 5.58 | 6.91 |
| 2 | 19.14 | 25.83 |
| 4 | 55.03 | 65.91 |
| 6 | 78.01 | 82.57 |
| 8 | 89.05 | 90.28 |
| 12 | 96.02 | 94.35 |

TABLE 9

In vitro dissolution profile of the memantine IR/SR granules of example 1.3.2

| T (hr) | pH 1.2 Mean Diss, % | pH 6.8 Mean Diss, % |
|---|---|---|
| 1 | 41.32 | 40.51 |
| 2 | 52.28 | 55.05 |
| 4 | 77.29 | 79.77 |
| 6 | 90.26 | 88.81 |

TABLE 9-continued

In vitro dissolution profile of the memantine IR/SR granules of example 1.3.2

| T (hr) | pH 1.2 Mean Diss, % | pH 6.8 Mean Diss, % |
|---|---|---|
| 8 | 95.12 | 92.01 |
| 12 | 98.34 | 94.22 |

3.3 Dissolution Profiles of Donepezil from the Oral Formulations 1 to 3

Dissolution profiles of donepezil from the oral formulations 1 to 3 are respectively summarized in Tables 10-12; while the memantine profiles are provided in Tables 13-15. Similar to findings in memantine IR/SR granules of examples 3.1 and 3.2, the dissolution profiles of both oral formulations 1 and 2 were pH-independent.

TABLE 10

In vitro dissolution profile of donepezil from oral formulation 1

| T (min) | pH 1.2 Mean Diss, % | pH 4.5 Mean Diss, % | pH 6.8 Mean Diss, % |
|---|---|---|---|
| 5 | 90.36 | 90.28 | 81.05 |
| 10 | 96.64 | 100.96 | 98.08 |
| 15 | 97.96 | 102.71 | 101.26 |
| 20 | 98.75 | 102.50 | 101.96 |
| 30 | 98.83 | 102.90 | 102.94 |

TABLE 11

In vitro dissolution profile of donepezil from oral formulation 2

| T (min) | pH 1.2 Mean Diss, % | pH 4.5 Mean Diss, % | pH 6.8 Mean Diss, % |
|---|---|---|---|
| 5 | 87.63 | 70.84 | 78.96 |
| 10 | 96.83 | 97.34 | 97.79 |
| 15 | 99.70 | 101.67 | 101.45 |
| 20 | 100.00 | 103.02 | 101.80 |
| 30 | 99.70 | 102.92 | 101.86 |

TABLE 12

In vitro dissolution profile of donepezil from oral formulation 3

| T (min) | pH 1.2 Mean Diss, % | pH 4.5 Mean Diss, % | pH 6.8 Mean Diss, % |
|---|---|---|---|
| 5 | 95.48 | — | — |
| 10 | 104.59 | — | — |
| 15 | 105.28 | — | — |
| 20 | 105.51 | — | — |
| 30 | 105.30 | — | — |

—: not determined.

TABLE 13

In vitro dissolution profile of memantine from oral formulation 1

| T (hr) | pH 1.2 Mean Diss, % | pH 4.5 Mean Diss, % | pH 6.8 Mean Diss, % |
|---|---|---|---|
| 0.5 | 35.25 | 34.81 | 35.44 |
| 1 | 37.94 | 36.77 | 38.62 |
| 2 | 48.13 | 48.80 | 51.44 |
| 4 | 73.01 | 76.22 | 77.82 |
| 6 | 85.69 | 87.37 | 88.56 |

TABLE 13-continued

In vitro dissolution profile of memantine from oral formulation 1

| T (hr) | pH 1.2 Mean Diss, % | pH 4.5 Mean Diss, % | pH 6.8 Mean Diss, % |
|---|---|---|---|
| 8 | 89.73 | 91.42 | 92.85 |
| 12 | 93.55 | 93.84 | 95.97 |

TABLE 14

In vitro dissolution profile of memantine from oral formulation 2

| T (hr) | pH 1.2 Mean Diss, % | pH 4.5 Mean Diss, % | pH 6.8 Mean Diss, % |
|---|---|---|---|
| 0.5 | 37.01 | 37.59 | 37.65 |
| 1 | 42.12 | 42.78 | 42.84 |
| 2 | 56.88 | 61.31 | 61.40 |
| 4 | 83.70 | 88.96 | 89.09 |
| 6 | 93.12 | 96.55 | 96.70 |
| 8 | 95.67 | 98.14 | 98.28 |
| 12 | 97.21 | 99.81 | 99.96 |

TABLE 15

In vitro dissolution profile of memantine from oral formulation 3

| T (hr) | pH 1.2 Mean Diss, % | pH 4.5 Mean Diss, % | pH 6.8 Mean Diss, % |
|---|---|---|---|
| 0.5 | 43.34 | — | 43.40 |
| 1 | 46.15 | — | 46.30 |
| 2 | 56.76 | — | 57.19 |
| 4 | 79.40 | — | 78.49 |
| 6 | 91.08 | — | 88.89 |
| 8 | 95.59 | — | 94.65 |
| 12 | 99.08 | — | 99.33 |

—: not determined.

Example 4 Pilot Pharmacokinetic (PK) Study of Donepezil/Memantine Oral Formulations 1 and 2

Pilot PK study was carried out in Chinese subjects, each receiving a single-dose medication, either positive control formulation or the respective donepezil/memantine oral formulations of example 1.4; PK properties of memantine and donepezil in each test subjects were then measured and recorded, as well as incidences and severities of undesirable side effects associated therewith.

This open-label, single-center randomized trial was conducted by Rosetta Pharmamate Co Ltd (Taipei, Taiwan) at Taipei Medical University—Shuang Ho Hospital (New Taipei City, Taiwan). Nineteen healthy adult Chinese subjects aged between 21 to 41 years old (the average is 30.4 years old) who met the inclusion and/or exclusion criteria as listed below were enrolled with informed consent.

Inclusion criteria:
1. Subjects are adults in good health as evidenced by medical history, physical examination, electrocardiogram, chest X-ray, and routine laboratory evaluation;
2. Each subject has a Body Mass Index (BMI) of 18.5 to 30.0 Kg/m$^2$. For male subject, body weight is above 50 Kg, for female subjects, body weight is above 45 Kg;

3. Vital sign (after 3 minutes resting in upright position) that are within the following ranges:
   Ear body temperature: ≥35.0° C. and ≤37.5° C.;
   Systolic blood pressure: ≥90 mmHg and ≤140 mmHg;
   Diastolic blood pressure: ≥50 mmHg and ≤90 mmHg;
   Pulse rate: ≥50 bpm and ≤90 bpm;
   Fasting blood sugar: ≤110 mg/dL;
4. Able to sign informed consent prior to study; and
5. Able to communicate well with the investigator and comply with the requirements of the study.

Exclusion Criteria:
1. Use of any prescription medication within 2 weeks prior to dosing;
2. Use of over-the-counter medications or vitamins within 2 weeks prior to dosing;
3. Significant illness within 2 weeks prior to dosing;
4. Participation in any clinical investigation within 2 months prior to dosing or longer as required by local regulation;
5. Blood donation or loss of blood of more than 500 mL within 3 months prior to the study. Blood donation or loss of blood of more than 250 mL within 2 months prior to the study;
6. History and/or physical findings of disorders, including cardiovascular disease, gastrointestinal disease, asthma and lung disease, neurological disease, psychiatric disease and etc;
7. History and/or physical findings of liver disease or liver injury by an abnormal liver function profile such as AST, ALT, γ-GT, Alkaline phosphatase or total Bilirubin;
8. History and/or physical findings of impaired renal functions as indicated by abnormal creatinine or BUN values or abnormal urinary constituents;
9. History of alcohol or drug abuse within 12 months prior to dosing; and
10. Pregnant or lactating women.

The enrolled subjects were randomly allocated to three groups according to a computer-generated randomization schedule. Each subject in Group 1 receive a positive control medicine (i.e., the immediate-release formulation of memantine and donepezil); whereas each subjects in Groups 2 and 3 respectively receive the capsules of Example 1.4, which corresponded to oral formulations 1 and 2. All subjects were required to fast for at least 10 hours prior to the administration of the medication so as to avoid any effects that might have been caused by food intake on the PK properties.

In Group 1, EBIXA® (containing 10 mg of memantine HCl, from H. Lundbeck A/S) and ARICEPT® (containing 5 mg of donepezil HCl, from Eisai) were orally administered to each subject, followed by another dose of EBIXA® (10 mg) administered twelve hours after the initial administration. As to subjects in Groups 2 and 3, they were respectively given oral formulations 1 and 2 of Example 1.4. Blood samples were drawn from each subject at pre-designated time points and plasma concentrations of memantine and donepezil were determined by HPLC-MS/MS.

PK properties including maximal plasma concentration ($C_{max}$), time to reach the peak concentration ($T_{max}$), time required for the plasma drug concentration to decrease by one half ($T_{1/2}$), the average time for the drug molecules to reside in the body (mean residence time, MRT), the area under the plasma concentration verses time curve from zero to the last measured time point ($AUC_{0-t}$), and the area under the plasma concentration verses time curve from zero to infinity ($AUC_{0-\infty}$) were assessed immediately before (0 hour) and at 0.5, 1, 2, 3, 4, 5, 6, 8, 10, 12, 12.5, 13, 14, 15, 16, 17, 18, 20, 22, 24, 36, 60, 84, 132, 180, 252 and 324 hours after drug administration.

$C_{max}$ and $T_{max}$ were obtained directly by the visual inspection of each subjects' plasma concentration-time profile. The slope of the terminal log-linear portion of the concentration-time profile was determined by least-squares regression analysis and used as the elimination rate constant (K). $T_{1/2}$ was obtained from the formula, $t_{1/2}=\ln(2)/K$. The $AUC_{0-t}$ from time zero to the last measured time point (i.e., 324 hours after the initial administration) was calculated using the trapezoidal rule and the extrapolated AUC from the last measured time point to infinity ($AUC_{0-\infty}$) was to be determined as the ratio of the last measured concentration ($C_t$) to the elimination rate constant. The area under the plasma concentration-time from zero to infinity ($AUC_{0-\infty}$) was calculated as the sum of the $AUC_{0-t}$ plus the ratio of $C_t/K$. MRT is calculated as the ratio of $AUMC_{0-\infty}$ to $AUC_{0-\infty}$ (i.e., $AUMC_{0-\infty}/AUC_{0-\infty}$), in which $AUMC_{0-\infty}$ is the area under the plasma (first) moment concentration-time curve from time zero to infinity, calculated by the trapezoidal rule and extrapolated to infinity.

The thus-obtained PK properties of donepezil and memantine of each groups are summarized in Tables 16 and 17.

TABLE 16

PK Properties of donepezil

| Subject No. | $T_{max}$ (h) | $C_{max}$ (ng/mL) | $T_{1/2}$ (h) | $AUC_{0-t}$ (h * ng/mL) | $AUC_{0-\infty}$ (h * ng/mL) | MRT (h) |
|---|---|---|---|---|---|---|
| Group 1 - Reference drug ||||||||
| 101 | 2.00 | 11.547 | 141.96 | 355.1 | 406.3 | 141.50 |
| 105 | 2.00 | 9.172 | 132.22 | 598.4 | 697.2 | 157.40 |
| 108 | 1.00 | 7.777 | 74.15 | 280.5 | 302.8 | 87.05 |
| 112 | 3.00 | 6.855 | 82.70 | 271.7 | 297.5 | 91.87 |
| 115 | 4.00 | 7.342 | 105.50 | 451.7 | 501.1 | 134.74 |
| 117 | 2.00 | 11.150 | 114.77 | 627.5 | 696.2 | 126.32 |
| 119 | 2.00 | 12.852 | 133.47 | 617.4 | 720.3 | 155.31 |
| Mean | 2.29 | 9.528 | 112.11 | 457.5 | 517.3 | 127.74 |
| SD | 0.95 | 2.341 | 26.17 | 158.5 | 188.2 | 28.35 |
| CV (%) | 41.6 | 24.6 | 23.3 | 34.6 | 36.4 | 22.2 |
| Median | 2.00 | 9.172 | 114.77 | 451.7 | 501.1 | 134.74 |
| Group 2 - oral formulation 1 ||||||||
| 103 | 3.00 | 7.707 | 82.85 | 463.3 | 489.6 | 99.69 |
| 106 | 2.00 | 12.371 | 105.77 | 703.8 | 790.5 | 138.36 |
| 107 | 3.00 | 7.648 | 101.66 | 451.6 | 502.5 | 135.70 |
| 111 | 2.00 | 8.942 | 102.62 | 550.9 | 618.7 | 134.77 |
| 113 | 3.00 | 6.780 | 100.34 | 542.9 | 612.2 | 139.78 |
| 116 | 2.00 | 10.040 | 110.71 | 573.0 | 640.4 | 134.05 |
| Mean | 2.50 | 8.915 | 100.66 | 547.6 | 609.0 | 130.39 |
| SD | 0.55 | 2.041 | 9.48 | 91.0 | 109.2 | 15.20 |
| CV (%) | 21.9 | 22.9 | 9.4 | 16.6 | 17.9 | 11.7 |
| Median | 2.50 | 8.325 | 102.14 | 546.9 | 615.4 | 135.23 |
| Group 3 - oral formulation 2 ||||||||
| 102 | 2.00 | 9.974 | 78.67 | 279.0 | 302.0 | 85.58 |
| 104 | 2.00 | 7.925 | 132.37 | 477.1 | 575.8 | 173.07 |
| 109 | 1.00 | 12.410 | 98.23 | 360.6 | 424.5 | 117.56 |
| 110 | 3.00 | 9.241 | 92.54 | 476.6 | 524.4 | 123.59 |
| 114 | 2.00 | 6.782 | 82.29 | 365.0 | 393.2 | 111.62 |
| 118 | 2.00 | 8.781 | 169.47 | 498.5 | 634.5 | 203.36 |
| Mean | 2.00 | 9.186 | 108.93 | 409.5 | 475.7 | 135.80 |
| SD | 0.63 | 1.926 | 35.28 | 87.6 | 124.3 | 43.68 |
| CV (%) | 31.6 | 21.0 | 32.4 | 21.4 | 26.1 | 32.2 |
| Median | 2.00 | 9.011 | 95.38 | 420.8 | 474.4 | 120.58 |

TABLE 17

PK Properties of Memantine

| Subject No. | $T_{max}$ (h) | $C_{max}$ (ng/mL) | $T_{1/2}$ (h) | $AUC_{0-t}$ (h * ng/mL) | $AUC_{0-\infty}$ (h * ng/mL) | MRT (h) |
|---|---|---|---|---|---|---|
| Group 1 - Reference drug | | | | | | |
| 101 | 14.00 | 28.834 | 54.78 | 2266.9 | 2303.0 | 67.96 |
| 105 | 14.00 | 23.785 | 78.09 | 2174.0 | 2301.0 | 101.84 |
| 108 | 15.00 | 27.326 | 69.56 | 2472.9 | 2583.9 | 94.11 |
| 112 | 15.00 | 23.925 | 48.50 | 1458.8 | 1485.3 | 50.24 |
| 115 | 15.00 | 27.691 | 75.37 | 2119.9 | 2223.0 | 91.38 |
| 117 | 14.00 | 32.740 | 40.34 | 1946.5 | 1977.2 | 54.88 |
| 119 | 14.00 | 26.266 | 50.63 | 2002.2 | 2071.2 | 65.86 |
| Mean | 14.43 | 27.224 | 59.61 | 2063.0 | 2134.9 | 75.18 |
| SD | 0.53 | 3.079 | 14.65 | 318.2 | 345.5 | 20.43 |
| CV (%) | 3.7 | 11.3 | 24.6 | 15.4 | 16.2 | 27.2 |
| Median | 14.00 | 27.326 | 54.78 | 2119.9 | 2223.0 | 67.96 |
| Group 2 - Oral formulation 1 | | | | | | |
| 103 | 13.00 | 19.368 | 60.39 | 1747.5 | 1778.1 | 77.01 |
| 106 | 24.00 | 20.246 | 64.51 | 2084 | 2154.7 | 94.08 |
| 107 | 15.00 | 21.117 | 53.25 | 2191.5 | 2227.5 | 84.62 |
| 111 | 13.00 | 24.862 | 53.32 | 2074.6 | 2105.9 | 79.25 |
| 113 | 14.00 | 17.040 | 83.69 | 1970.2 | 2113.2 | 119.98 |
| 116 | 14.00 | 20.741 | 63.05 | 2257.4 | 2325.4 | 94.21 |
| Mean | 15.50 | 20.562 | 63.04 | 2054.2 | 2117.5 | 91.53 |
| SD | 4.23 | 2.560 | 11.19 | 180.3 | 185.5 | 15.7 |
| CV (%) | 27.3 | 12.4 | 17.8 | 8.8 | 8.8 | 17.2 |
| Median | 14.00 | 20.494 | 61.72 | 2079.3 | 2133.9 | 89.35 |
| Group 3 - Oral formulation 2 | | | | | | |
| 102 | 15.00 | 20.707 | 52.50 | 1902.1 | 1930.9 | 78.91 |
| 104 | 14.00 | 19.008 | 71.44 | 1780.4 | 1855.7 | 100.24 |
| 109 | 14.00 | 27.157 | 46.46 | 2250.7 | 2273.0 | 74.49 |
| 110 | 14.00 | 31.428 | 60.08 | 3000.3 | 3073.9 | 91.00 |
| 114 | 14.00 | 20.622 | 60.71 | 1630.2 | 1659.1 | 74.13 |
| 118 | 15.00 | 23.323 | 59.33 | 1821.9 | 1870.8 | 85.71 |
| Mean | 14.33 | 23.708 | 58.42 | 2064.3 | 2110.6 | 84.08 |
| SD | 0.52 | 4.738 | 8.44 | 503.0 | 512.4 | 10.29 |
| CV (%) | 3.6 | 20.0 | 14.5 | 24.4 | 24.3 | 12.2 |
| Median | 14.00 | 22.015 | 59.71 | 1862.0 | 1900.9 | 82.31 |

Results summarized in Tables 16 revealed that PK properties of donepezil derived from subjects administered with oral formulations 1 and 2 of this disclosure were similar to those derived from positive control subjects, i.e., subjects administered with commercially available donepezil-containing formulation (i.e., ARICEPT) indicating that at least the PK properties for the immediate-release portion of the oral formulation of this invention is comparable to the control medicine, which is also a fast-release formulation. In addition to the $C_{max}$, the $AUC_{0-t}$ and $AUC_{0-\infty}$ of donepezil in these three groups are also comparable to one another.

As to the SR portion, data in Table 17 revealed that the mean maximal plasma concentrations ($C_{max}$) of memantine derived from subjects administered with oral formulation 1 (i.e., Group 2 subjects; mean $C_{max}$=20.562 ng/mL) or oral formulation 2 (i.e., Group 3 subjects; mean $C_{max}$=23.708 ng/mL) are lower than that of the control subjects, or subjects administered with EBIXA® (i.e., Group 1 subjects; mean $C_{max}$=27.224 ng/mL). Also, the median $C_{max}$ of memantine derived from Group 2 subjects (median $C_{max}$=20.494 ng/mL) or Group 3 subjects (median $C_{max}$=22.015 ng/mL) are lower than that of Group 1 subjects (median $C_{max}$=27.326 ng/mL).

Further, the time required reaching the peak concentration ($T_{max}$) of memantine in subjects administered with oral formulation 1 (mean $T_{max}$=15.5; median $T_{max}$=14) is longer than that of the control subjects (Group 1; mean $T_{max}$=14.43; median $T_{max}$=14), whereas $T_{max}$ for subject administered with oral formulation 2 (mean $T_{max}$=14.33; mean $T_{max}$=14) is shorter than that of the control subjects.

In contrast, data summarized in Table 16 revealed that the $AUC_{0-t}$ and the $AUC_{0-\infty}$ of memantine derived from subjects taking either oral formulation 1 or oral formulation 2 are quite similar to those derived from control subjects, i.e., subjects administered with EBIXA®, which suggest that the oral formulations 1 and 2 of this disclosure respectively possess similar therapeutic effect as that of EBIXA®.

In view of the foregoing, the formulation as well as the method of the present disclosure may achieve the desired therapeutic effect.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

We claim:

1. An oral dosage formulation comprising a sustained-release portion of memantine; and an immediate-release portion of donepezil and/or memantine, in which the oral dosage formulation is characterized in having a pH-independent dissolution profile of memantine from about pH 1.0 to 7.2; and the oral dosage formulation has ingredients as set forth below:

| | Ingredients | Weight (mg) | Percentage (%) |
|---|---|---|---|
| donepezil/memantine IR granules | Donepezil HCl | 5 | 4.5 |
| | Memantine HCl | 8 | 7.3 |
| | Microcrystalline cellulose | 85.9 | 78.1 |
| | Pregelatinized Starch | 10.0 | 9.1 |
| | Magnesium stearate | 1.1 | 1 |
| | Subtotal | 110 | 100 |
| memantine SR granules | Memantine HCl | 12 | 13.06 |
| | Sugar sphere | 60 | 65.29 |
| | Hydroxypropyl methyl cellulose (HPMC) | 6 | 6.53 |
| | Polyethylene glycol | 1.2 | 1.31 |
| | Ethyl cellulose | 12.7 | 13.82 |
| | Subtotal | 91.9 | 100. |

2. A method of treating dementia or Alzheimer's disease in a subject, comprising:
   administering to the subject the oral dosage formulation of claim 1.

3. The method of claim 2, wherein the oral dosage formulation is administered to the subject once a day or once every two days.

* * * * *